(12) United States Patent
Kuo et al.

(10) Patent No.: US 8,559,003 B2
(45) Date of Patent: Oct. 15, 2013

(54) ELECTRICALLY DRIVEN DEVICES FOR SURFACE ENHANCED RAMAN SPECTROSCOPY

(76) Inventors: Huei Pei Kuo, Cupertino, CA (US); Shih-Yuan Wang, Palo Alto, CA (US); Min Hu, Sunnyvale, CA (US); Zhiyong Li, Redwood City, CA (US); Alexandre M. Bratkovski, Mountain View, CA (US)

( * ) Notice: Subject to any disclaimer, the term of this patent is extended or adjusted under 35 U.S.C. 154(b) by 0 days.

(21) Appl. No.: 13/384,456

(22) PCT Filed: Sep. 17, 2009

(86) PCT No.: PCT/US2009/057327
§ 371 (c)(1),
(2), (4) Date: Jan. 17, 2012

(87) PCT Pub. No.: WO2011/034533
PCT Pub. Date: Mar. 24, 2011

(65) Prior Publication Data
US 2012/0113420 A1 May 10, 2012

(51) Int. Cl.
*G01J 3/44* (2006.01)
(52) U.S. Cl.
USPC .......................................................... 356/301
(58) Field of Classification Search
USPC .......................................................... 356/301
See application file for complete search history.

(56) References Cited

U.S. PATENT DOCUMENTS

| | | | |
|---|---|---|---|
| 5,194,913 A * | 3/1993 | Myrick et al. | 356/301 |
| 6,970,239 B2 | 11/2005 | Chan et al. | |
| 7,075,642 B2 * | 7/2006 | Koo et al. | 356/301 |
| 7,224,451 B2 | 5/2007 | Naya | |
| 7,321,422 B2 | 1/2008 | Li et al. | |
| 7,351,588 B2 | 4/2008 | Poponin | |
| 7,361,313 B2 | 4/2008 | Chan et al. | |
| 7,391,511 B1 * | 6/2008 | Bratkovski et al. | 356/301 |
| 7,400,395 B2 | 7/2008 | Chan et al. | |
| 7,450,227 B2 | 11/2008 | Dwight et al. | |
| 7,456,012 B2 | 11/2008 | Ryttsen et al. | |
| 7,476,501 B2 | 1/2009 | Chan et al. | |
| 7,476,787 B2 | 1/2009 | Thomas et al. | |
| 7,995,201 B2 | 8/2011 | Bratkovski et al. | |
| 8,017,408 B2 | 9/2011 | Meinhart et al. | |

(Continued)

FOREIGN PATENT DOCUMENTS

JP       2006349463       12/2006

OTHER PUBLICATIONS

Branston et al. "Field Emission From Metal-Coated Silicon Tips", IEEE Transactions on Electron Devices, vol. 38, No. 10, Oct. 1991, pp. 2329-2333.

(Continued)

*Primary Examiner* — Gregory J Toatley
*Assistant Examiner* — Shawn Decenzo (57) ABSTRACT

An electrically driven device for surface enhanced Raman spectroscopy includes a first electrode, a substrate positioned proximate to the first electrode, a plurality of cone shaped protrusions formed integrally with or on a substrate surface, a Raman signal-enhancing material coated on each protrusion, and a second electrode positioned relative to the first electrode at a predetermined distance. Each of the protrusions has a tip with a radius of curvature ranging from about 0.1 nm to about 100 nm. The second electrode is positioned relative to the first electrode such that the electrodes together produce an electric field when a voltage bias is applied therebetween. The electric field has a field distribution that creates a stronger field gradient at a region proximate to the tips than at other portions of the substrate.

11 Claims, 10 Drawing Sheets (56) References Cited

U.S. PATENT DOCUMENTS

| | | | |
|---|---|---|---|
| 2003/0059820 A1* | 3/2003 | Vo-Dinh | 435/6 |
| 2008/0074662 A1 | 3/2008 | Gu et al. | |
| 2008/0137081 A1* | 6/2008 | Murakami | 356/301 |
| 2009/0148729 A1 | 6/2009 | Mills | |
| 2010/0143744 A1* | 6/2010 | Gupta et al. | 428/601 |
| 2011/0228266 A1* | 9/2011 | Kuo et al. | 356/301 |
| 2012/0113418 A1 | 5/2012 | Fattal et al. | |

OTHER PUBLICATIONS

Cao, et al., "Enhanced Raman Scattering from Individual Semiconductor Nanocones and Nanowires", Physical Review Letters, The American Physical Society, pp. 157402-1-4, Apr. 21, 2006.

Guieu, Valerie, et al., "Multitip-Localized Enhanced Raman Scattering from a Nanostructured Optical Fiber Array", J. Phys. Chem. C 2009, vol. 113, pp. 874-881, Published online Dec. 31, 2008.

Hu et al. "Metal Coated Si Nanogras as Highly Sensitive SERS Sensors", Proc. of SPIE, vol. 7312, pp. 731201-1-731201-6.

Tang et al. "Silver-Coated Si Nanograss as Highly Sensitive Surface-Enhanced Raman Spectroscopy Substrates", Applied Physics A, Published online: Jun. 27, 2009 (5 pages).

Algar, Russ, et al. "The application of quantum dots, gold nanoparticles and molecular switches to optical nucleic-acid diagnostics." TrAC Trends in Analytical Chemistry 28.3 (2009): 292-306.

Sassolas, A. et al. DNA Biosensors and Microarrays, (Research Paper), Jun. 21, 2007, pp. 109-139, vol. 108, No. 1.

* cited by examiner

ELECTRICALLY DRIVEN DEVICES FOR SURFACE ENHANCED RAMAN SPECTROSCOPY

BACKGROUND

The present disclosure relates generally to electrically driven devices for surface enhanced Raman spectroscopy.

Raman spectroscopy is used to study the transitions between molecular energy states when photons interact with molecules, which results in the energy of the scattered photons being shifted. The Raman scattering of a molecule can be seen as two processes. The molecule, which is at a certain energy state, is first excited into another (either virtual or real) energy state by the incident photons, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation photons. The Raman spectrum of different molecules or matters has characteristic peaks that can be used to identify the species. As such, Raman spectroscopy is a useful technique for a variety of chemical or biological sensing applications. However, the intrinsic Raman scattering process is very inefficient, and rough metal surfaces, various types of nano-antennas, as well as waveguiding structures have been used to enhance the Raman scattering processes (i.e., the excitation and/or radiation process described above). This field is generally known as surface enhanced Raman spectroscopy (SERS).

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figures 4A, 4B:
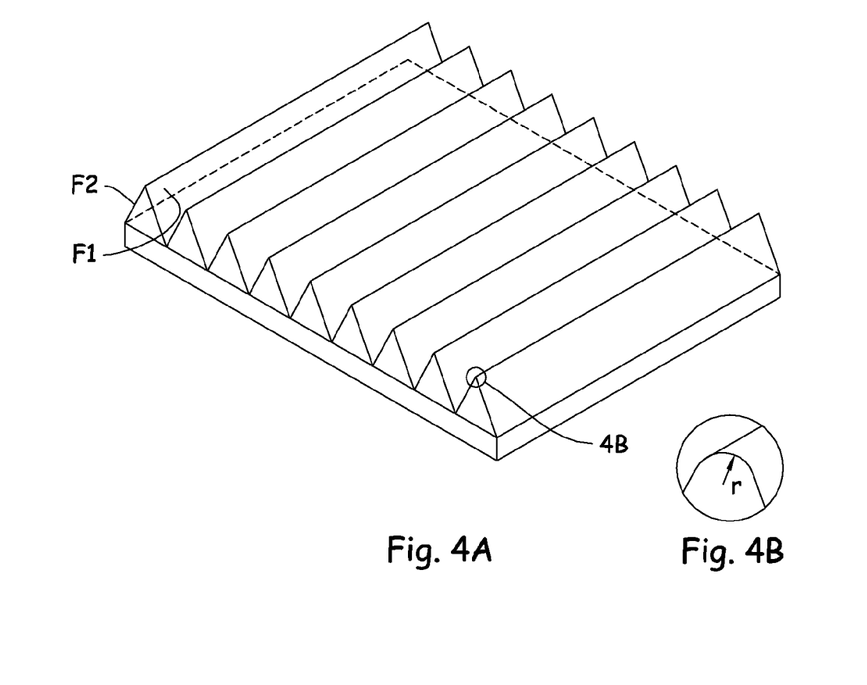
FIG. 4A is a perspective view of a comparative structure having knife-edge protrusions.
FIG. 4B is an enlarged view of one of the knife-edge protrusions of FIG. 4A, illustrating the radius of curvature (r) of the protrusion.

Embodiments of the device disclosed herein advantageously include a substrate having a plurality of cone shaped surface protrusions formed thereof or thereon. The protrusions have a radius of curvature that contributes to an enhanced electric field at the tip of such protrusions when a voltage bias is applied between the substrate and a counter electrode positioned near the protrusions. The electric field at the tip is enhanced by a factor ranging from 2 to 10,000 when compared to the electric field at substantially flat surfaces (i.e., any portion of the protrusion or substrate that has a radius of curvature that is larger than the radius of curvature of the protrusions) of the same device. This field distribution also creates a gradient of the field that is much stronger at the tips of the protrusions and in the regions proximate the tips. Furthermore, the electric field of the embodiments of the device disclosed herein is also much larger than the electric field of devices including ridge shaped or knife-edge shaped protrusions (which, for comparative purposes, is shown in FIGS. 4A and 4B). Under suitable conditions, the enhanced electric field and the field gradient advantageously concentrates analyte molecules (or other materials of interest) dispersed into the region above the protrusion side of the substrate. In turn, this concentration of analyte molecules (at and in the vicinity of the protrusion tips) amplifies the SERS signal emitted by the analyte molecules (or other material of interest). Still further, the optical field from an excitation illumination source may also be enhanced in the same regions.

In the embodiments disclosed herein, valleys are formed between the cone shaped protrusions. Generally, the valleys consist of those portions of the substrate that are substantially flat. In contrast, the regions of the substrate that are directly between two cone shaped protrusions are referred to herein as crevices, and such crevices may have dimensions that contribute to an enhanced optical field at these portions. Such crevices may have an inverted cone shape. It is believed that the enhanced optical field in the crevices may also facilitate a strong SERS signal.

Figure 1:
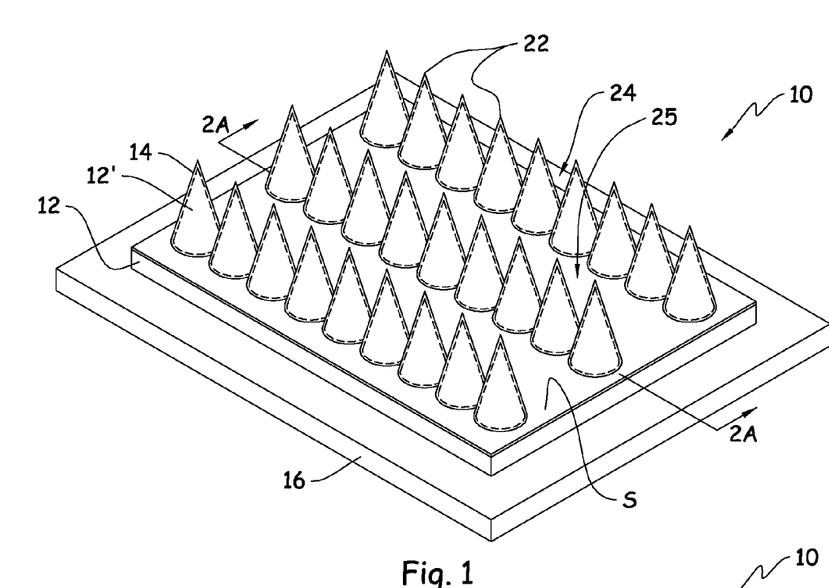
FIG. 1 is a perspective view of an embodiment of an electrically driven device with one of the electrodes removed for clarity.

Referring now to FIG. 1, a portion of an embodiment of electrically driven device 10 is depicted. The device includes a substrate 12. Non-limiting examples of suitable substrate 12 materials include single crystalline silicon, polymeric materials (acrylics, polycarbonates, polydimethylsiloxane (PDMS), polyimide, etc.), metals (aluminum, copper, stainless steel, alloys, etc.), quartz, ceramic, sapphire, silicon nitride, or glass. In some instances, after protrusions 12' (described further hereinbelow) are formed on the substrate 12, the incoming light may become trapped by the protrusions 12' by mechanisms such as multiple forward scattering or through continuous variation of the index of refraction. The trapped light renders the appearance of the substrate 12 dark or black. As such, the silicon substrate 12 having the protrusions 12' thereon may be referred to herein as "black silicon". The dimensions of the substrate 12 may vary, depending, at least in part, upon the desirable size of the resulting device 10 and upon the number and depth of the protrusions 12' to be formed.

Figures 2A, 2B:
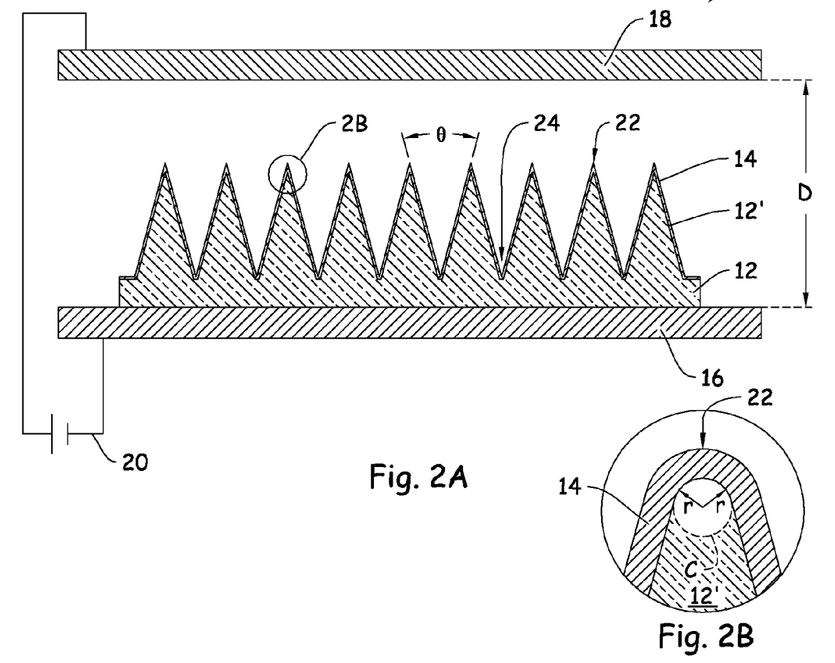
FIG. 2A is a cross sectional view, taken along line 2A-2A of FIG. 1, with the additional electrode and a power source shown.
FIG. 2B is an enlarged view of one of the protrusions of FIG. 2A, illustrating the radius of curvature (r) of the protrusion.

As shown in FIG. 1, the substrate 12 has cone shaped protrusions 12' integrally formed therewith. Such protrusions 12' may also be referred to as nano-grass or surface roughness. Each protrusion 12' has a radius of curvature (r) that is very small, ranging from about 0.1 nm to about 100 nm. Referring briefly to FIG. 2B, an enlarged view of the cross-section of the tip (labeled 22) of one of the protrusions 12' is shown. The radius of curvature (r) is also shown. The radius of curvature (r) is the radius of the approximate circle C that results when points are drawn on part of the curved portion of the protrusion 12'. Furthermore, compared to the substantially flat surfaces of the substrate 12, the total surface area of the protrusions 12' is larger by a factor ranging from 2 to 10, due to the cone shape of the tips 22. As a result of this increased surface area, more target molecules can be trapped on the substrate 12, and thus more Raman photons can contribute to the overall SERS signal.

Referring back to FIG. 1, the protrusions 12' are formed such that a valley 25 is formed at substantially flat areas of the substrate 12 where protrusions 12' are not formed, and crevices 24 are formed in the region proximate two adjacent protrusions 12'. A plurality of crevices 24 may resemble an ensemble of pits, each of which has a sharp point or angle θ (see FIG. 2A). In an embodiment, each crevice 24 is essentially the inverse of the apex/tip 22 of the protrusions 12'. In some instances, the point at the crevice 24 may be sharper than the point at the tip 22 of the adjacent protrusions 12'. The angle θ at each crevice 24 may be any angle up to 180°. In one non-limiting example, the desirable angle θ ranges from about 10° to about 20°.

In an embodiment, the protrusions 12' may be formed by deep reactive ion etching and passivation. More specifically, the Bosch process may be used, and this process involves a series of alternating cycles of etching (e.g., using $SF_6$ and $O_2$ plasmas) and passivation (e.g., using a $C_4F_8$ plasma). The morphology of the resulting protrusions 12' may be controlled by controlling the conditions (e.g., vacuum pressure, RF power, total processing time, individual etching cycle time, individual passivation cycle time, and gas flow rates) of the process. In one non-limiting example, the etcher is operated at a pressure of 15 mTorr, the coil and platen powers of the etcher are 800 W and 10 W, respectively, each etching cycle (with $SF_6$ and $O_2$) is 6 seconds, each passivation cycle (with $C_4F_8$) is 5 seconds, and the flow rates for $SF_6$, $O_2$, and $C_4F_8$ are 100 sccm, 13 sccm, and 100 sccm, respectively. More generally, the flow rate may be any rate up to about 100 sccm.

In another embodiment, the protrusions 12' may be formed using nanoimprinting techniques. In one embodiment, a nanoimprint mold or master (not shown) may be used to form the protrusions 12'. The nanoimprint mold includes a base and a plurality of features formed in a surface of the base. The features of the mold are configured so that when the nanoimprint mold is utilized to imprint the substrate 12, the features define the desired protrusions 12'. As such, the features of the mold are a negative replica (or the inverse) of the protrusions 12'. A double molding process may be used to produce a positive replica.

The mold base may be include silica, silicon, quartz, gallium arsenide, or any other suitable metal, ceramic, or polymer material. The features of the mold may be formed in the surface of the mold base by for example, using electron beam lithography, reactive ion etching, or any other wet or dry chemical etching method that results in the formation of a plurality of depressions or grooves in the surface of the mold base. In one embodiment, the mold itself may be formed via the etching and passivation process previously described.

Additionally, a two-generation mastering process may be used to create the mold/master that is the inverse of the substrate 12 having protrusions 12' formed therein. In this embodiment, the substrate 12 and protrusions 12' is created via etching and passivation, and then the mold/master may be formed using the substrate 12.

When the protrusions 12' in the substrate 12 are formed via nanoimprinting, the substrate 12 is a deformable material (e.g., a polymer, such as polymethylmethacrylate (PMMA) or any other commercially available nanoimprint resist material). This deformable substrate material may solidify upon application of energy (such as radiation or heat) thereto. Such nanoimprint lithography resists are sold by, for example, Nanonex of Monmouth Junction, N.J.

The nanoimprint mold is pressed into the substrate 12 to form corresponding peaks (i.e., protrusions 12') and grooves (i.e., crevices 24) therein. In this embodiment, the imprinted substrate 12 may be cured to solidify the protrusions 12', and the nanoimprint mold may be separated from the substrate 12.

Even though the cone shaped protrusions 12' are formed integrally with the substrate 12, it is to be understood that the protrusions 12' may be formed of the same material as the substrate 12 or of different materials. In one non-limiting example, the protrusions 12' are composed of silicon with a passivating fluorocarbon polymer layer formed thereon. In another non-limiting example, the protrusions 12' are composed of a polymeric material, while the substrate 12 is composed of glass, quartz, silicon nitride, metal, or any combination thereof.

Regular or non-regular arrays of the protrusions 12' may be formed. The etching and passivation process previously described often results in a non-regular array. It is to be understood that in order to generate a regular array, a fabrication method, such as focused ion-beam, e-beam lithography, optical lithography, or nanoimprint lithography may be used.

As shown in FIG. 1, the protrusions 12' also have a Raman signal-enhancing material 14 coated thereon. It is to be understood that the phrase "Raman signal-enhancing material" as used herein means a material that, when established on the protrusions 12', is capable of increasing the number of Raman scattered photons when the analyte (or other material of interest) is located proximate to that protrusion 12', and when the analyte and material are subjected to electromagnetic radiation. Raman signal-enhancing materials include, but are not limited to, silver, gold, and copper.

The Raman signal-enhancing material 14 may be established by any suitable deposition or other coating technique. A blanket deposition technique may be used so that the material 14 is established on all of the exposed portions of the surface S of the substrate 12. As a non-limiting example, the material 14 may be deposited via electron-beam (e-beam) evaporation or sputtering. In still another non-limiting example, the Raman signal-enhancing material 14 can be pre-formed nanoparticles (e.g., of silver or gold), which are coated onto the surface S.

After deposition of the material 14, each protrusion 12' remains substantially unchanged in terms of its tip/apex 22 angle and radius of curvature r, and in terms of its crevice 24 angle. A relatively uniform coating (often in the form of numerous small nanoparticles on the slopes and/or tips 22 of the protrusions 12') of the material 14 is produced. While shown as a continuous coating in FIG. 1, the material 14 may be deposited in the form of the previously mentioned nanoparticles (not shown). Such nanoparticles have an average diameter ranging from about 1 nm to about 200 nm. In one non-limiting example, the average nanoparticle diameter ranges from about 40 nm to about 100 nm. In another non-limiting example, the average nanoparticle diameter is equal to or less than 50 nm. It is believed that the presence of the material 14 nanoparticles (rather than a continuous coating of material 14) at the apex 22 further enhances the already enhanced electric field. The material 14 itself may also have a surface roughness that spontaneously forms during the deposition process. Such surface roughness can act as additional optical antennas to increases the SERS-active sites over each protrusion 12' and/or adjacent each protrusion 12'.

Referring now to FIGS. 1 and 2A together, the device 10 further includes two electrodes 16, 18 (note that electrode 18 is not shown in FIG. 1 for clarity). The first electrode 16 is positioned proximate to the substrate 12. The second electrode 18 is positioned relative to the first electrode 16 so that the two electrodes 16, 18 are positioned a desirable distance D (shown in FIG. 2A) from each other. It is to be understood that in one embodiment, the distance D is much larger than the radius of curvature (r), and the enhancement of the electric field at the tips 22 (which is discussed further in reference to FIG. 10) is weakly dependent upon the distance D. A smaller distance D generally creates a larger electric field. Thus, the distance D will depend, at least in part, on the desirable electric field at the tips 22 of the protrusions 12'.

As shown in FIG. 2A, the material 14 coated substrate 12 is positioned between the electrodes 16, 18. In one embodiment, the material 14 coated substrate 12 may be positioned directly on the electrode 16, and the other electrode 18 may be positioned above the material 14 coated substrate 12. The positioning of each of the electrodes 16, 18 and the material 14 coated substrate 12 is such that when an appropriate voltage bias is applied between the electrodes 16, 18, the electric field is enhanced at each tip/apex 22 of the protrusions 12'.

Since SERS applications involve light of a suitable wavelength being directed toward the substrate 12 (and in this particular disclosure, toward one or more of the protrusions 12'), it is desirable that the electrode 18, which is positioned such that it faces the apexes 22 of each protrusion 12', is at least partially transparent to such light. Non-limiting examples of suitable transparent electrodes include indium tin oxide electrodes, Al- and Ga-doped ZnO (AZO and GZO), carbon, or the like. The other electrode 16 may be transparent or opaque as long as light is not to be transmitted therethrough. Examples of other electrode materials include metals, such as gold, platinum, aluminum, silver, tungsten, copper, etc. The electrodes 16, 18 shown in FIG. 2A have rectangular cross-sections, but it is to be understood that electrodes 16, 18 may also have circular, elliptical, or more complex cross-sections. The electrodes 16, 18 may also have many different widths or diameters and aspect ratios or eccentricities. Still further, the electrodes 16, 18 may be hollow electrodes (see, for example, the ring electrode 18, 18' shown in FIG. 11) and/or plate electrodes.

Figure 3A:
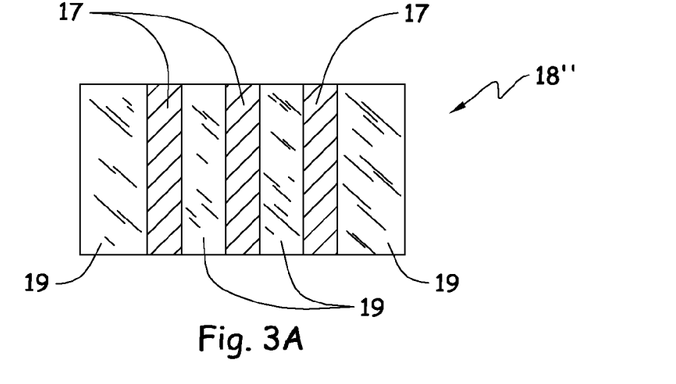
FIGS. 3A and 3B are top views of embodiments of partially transparent electrodes that are suitable for use in the devices disclosed herein.
Figure 3B:
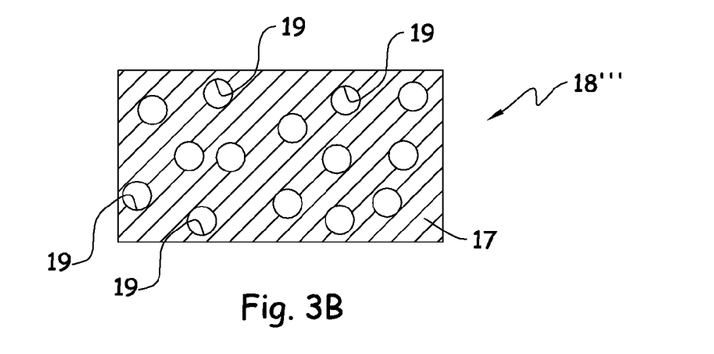

Examples of other electrodes 18" and 18''' are shown in FIGS. 3A and 3B, respectively. These electrodes 18", 18''' are partially transparent electrodes that include conductive portions 17 and optically transparent portions 19. The conductive portions 17 may be formed of any suitable conductive material, and the optically transparent portions 19 may be formed of any material that is transparent to the desirable excitation wavelengths and the resulting SERS signals. As shown in FIG. 3A, the electrode 18" includes conductive parallel or grid lines (i.e., conductive portions 17) formed on and/or between multiple optically transparent portions 19. In this embodiment, the conductive parallel lines are formed of an opaque metal (having a width ranging from about 1 μm to 10 μm) and are spaced at a distance ranging from about 10 μm to about 100 μm. This electrode 18" may be particularly suitable for instances when the distance D between the electrodes 16, 18 is greater than the spacing between the conductive lines. As shown in FIG. 3B, the electrode 18''' includes apertures (i.e., optically transparent portions 19) formed through a conductive material (i.e., conductive portion 17). When apertures are used as the optically transparent portions 19, it is to be understood that they may be left empty (i.e., filled with air) or may be filled with another optically transparent material. The size (e.g., diameter) of each aperture may range from about 10 μm to about 100 μm. Furthermore, the ratio of apertures (i.e., optically transparent portions 19) to conductive portion 17 may range anywhere from 1% to 99%. The configurations of the electrodes 18", 18''' shown in these Figures allow a fraction of the light introduced thereon to pass through to the underlying substrate 12 via the optically transparent portions 19.

The electrodes 16, 18 may be acquired in a usable state or may be fabricated using conventional techniques, such as photolithography or electron beam lithography, or by more advanced techniques, such as, e.g., imprint lithography.

It is to be understood that the electrodes 16, 18 and the substrate 12 may be any suitable size (ranging from a micrometer up to inches), and will depend, at least in part, upon the desirable SERS application for which it is being configured. In one embodiment, the size of each of the electrodes 16, 18 is comparable to the size of the substrate 12. It is to be understood that since the bottom electrode 16 is generally not used for light transmission, it may be thicker than the top electrode 18.

With reference to FIGS. 4-10, the principles of operation of the device 10 are described (FIGS. 5-6), and comparison of such operation is made to a device including protrusions with knife-edge geometry (FIGS. 4A, 4B, and 7-10). To reiterate, the device 10 disclosed herein includes the cone shaped protrusions 12'. In sharp contrast, the knife-edge geometry is shown in FIGS. 4A and 4B. The knife-edge protrusions generally include two facets $F_1$, $F_2$ that are joined together at a tip, and such facets extend the entire length of the substrate. The radius of the curvature (r) of the knife-edge geometry refers to the radius of curvature of the tip at the intersection of facets F1 and F2, as shown in FIG. 4B.

Figure 5:
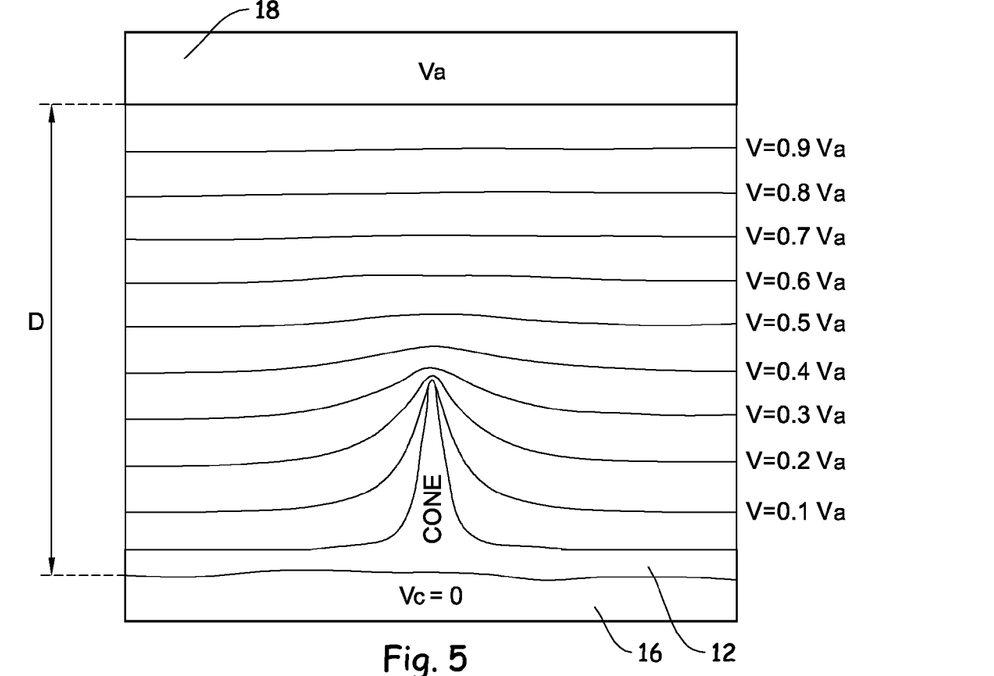
FIG. 5 is a schematic cross-sectional illustration of an embodiment of the device including a single cone shaped protrusion and the simulated equipotential lines at such protrusion upon application of various voltages.
Figure 6:
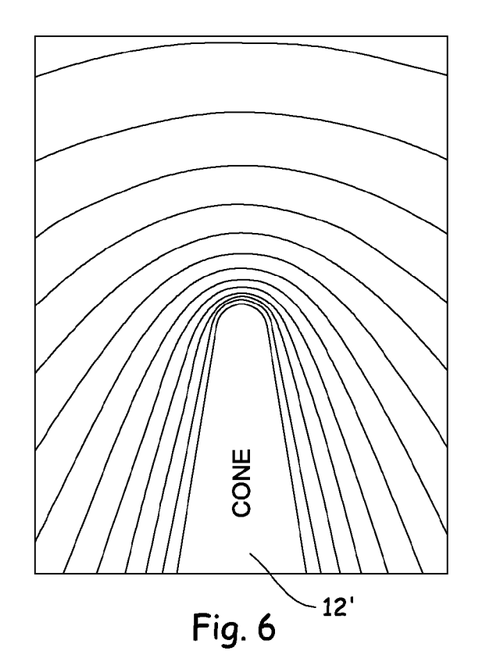
FIG. 6 is an enlarged, more detailed view of the illustration of FIG. 5.

Referring now specifically to FIGS. 5 and 6, cross-sectional views of a single cone shaped protrusion 12' are illustrated with a computed field distribution as a result of the application of a voltage $V_a$ on the electrode 18 and voltage $V_c$ on the electrode 16. In these examples, a voltage difference of magnitude $(V_a-V_c)$ is applied. As illustrated in the Figures, a voltage difference of $V_a$ is applied between the electrodes 16, 18 when the voltage $V_c$ is zero.

FIG. 5 illustrates the equi-potential lines of the cone shaped protrusion 12' on a flat substrate 12 and electrode 16. In this example, D/r=1000, and any suitable dimensions resulting in this ratio may be used in this simulation. As non-limiting examples, the separation distance D between the electrodes is 5 μm or 100 μm, while the radius of curvature is respectively 5 nm or 100 nm. The height of the protrusion 12' (for the simulation) is 2 μm when r=5 nm.

As previously mentioned, the voltage, Vc, is assumed to be zero. As illustrated in FIGS. 5 and 6, in a region away from the tip 22 of the protrusion 12', the equi-potential lines are substantially spaced apart and the field is substantially uniform and equal, i.e., $V_a/D$, where $V_a$ is the voltage on the electrode 18. At the tip 22 however, the field is enhanced. This enhancement is indicated by the crowding of the equi-potential lines at the tip 22 (shown more clearly in FIG. 6). In FIG. 6, the voltage difference between neighboring lines at the tip 22 is $0.002V_a$.

The magnitude of the electrostatic field at the surface of the tip 22 of the cone shaped protrusion 12' is approximately 100 times higher than the field at the flat region of the substrate 12. In other words, the field strength at the tip 22 is enhanced by a factor of about 100 for the selected tip curvature r. It is to be understood that the field generated may be a DC field, which is static, or an AC field, which is time varying.

As illustrated, the equi-potential lines of the electric field converge and concentrate at and near the tip 22, and thus the gradient of the electric field at and near the protrusion 12' is accentuated. The gradient of the electric field provides an attractive force on polarizable analyte molecules toward the high field region. The force is proportional to the gradient and is attractive toward the high field region. Thus, polarizable molecule(s) with permanent dipoles are attracted toward the tips 22 and regions of the cones 12' proximate to the tips 22. For molecules with a permanent charge, the force on the molecule is proportional to the field. The direction of the force is dependent on the charge polarity. For example, $V_a$ can be biased negatively to attract a positively charged analyte molecule toward the tips 22 of the protrusions 12'. This results in an increased number of analyte molecules at the tip 22, which will, in turn, enhance the SERS signal.

Figure 7:
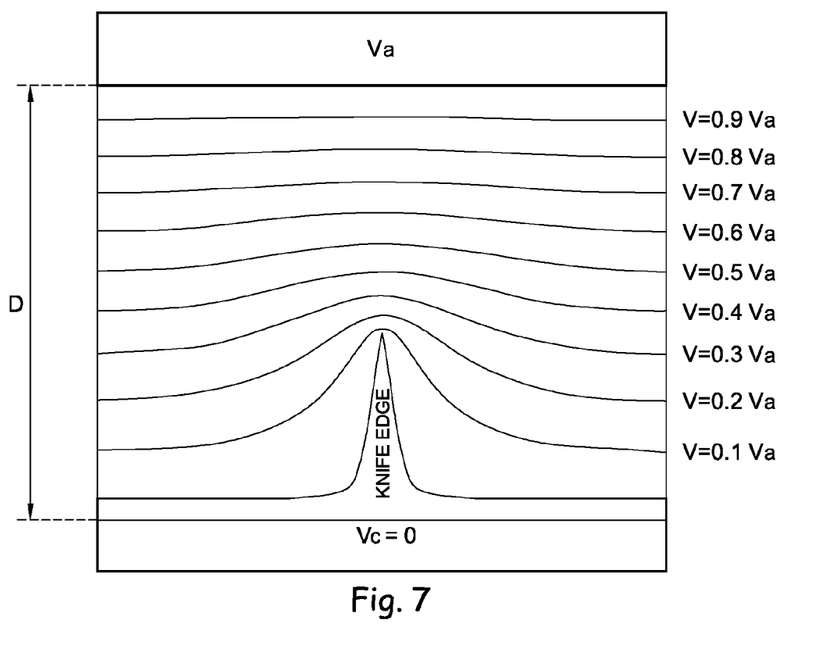
FIG. 7 is a schematic cross-sectional illustration of a comparative device including a single knife-edge protrusion and the simulated equipotential lines at such protrusion upon application of various voltages.
Figure 8:
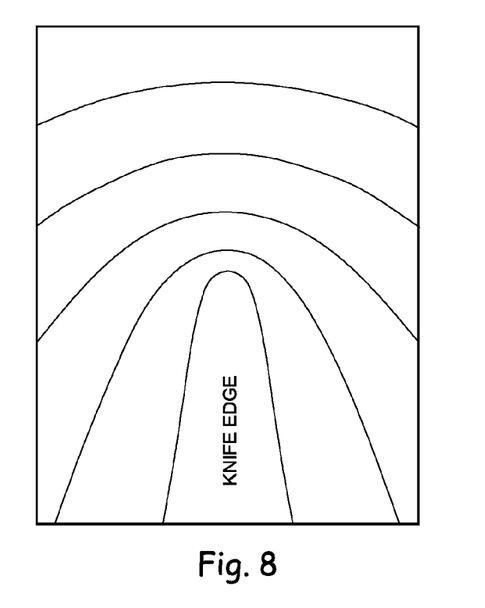
FIG. 8 is a schematic cross-sectional illustration of a comparative device including a single knife-edge protrusion and the simulated equipotential lines at the tip of such protrusion upon application of various voltages.

For comparative purposes, the field and gradient for one of the knife-edge protrusions are shown in FIGS. 7 and 8. The field distribution is shown in FIG. 7, and the details at the tip are shown more clearly in FIG. 8. In comparing the field distribution of the embodiment of the cone-shaped protrusion 12' disclosed herein and the comparative knife-edge protrusion under the same physical configuration (i.e., the distance between the electrodes 16, 18 is the same) and applied voltage bias, the field in the vicinity of the cone-shaped protrusion is higher than in the vicinity of the knife-edge protrusion. The comparison between FIG. 6 and FIG. 8 shows that the electrostatic field is much higher near the tip 22 of the cone-shaped protrusion 12' than the field near the tip of the knife-edge protrusion.

Figure 9:
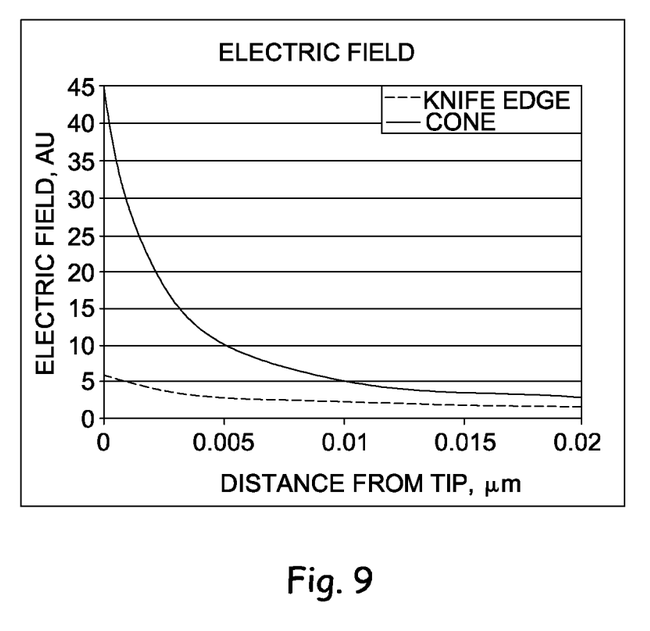
FIG. 9 is a graph comparing the simulated electric fields for the embodiment of the device including a single cone-shaped protrusion and the comparative device including a single knife-edge protrusion discussed in reference to FIGS. 5-8.
Figure 10:
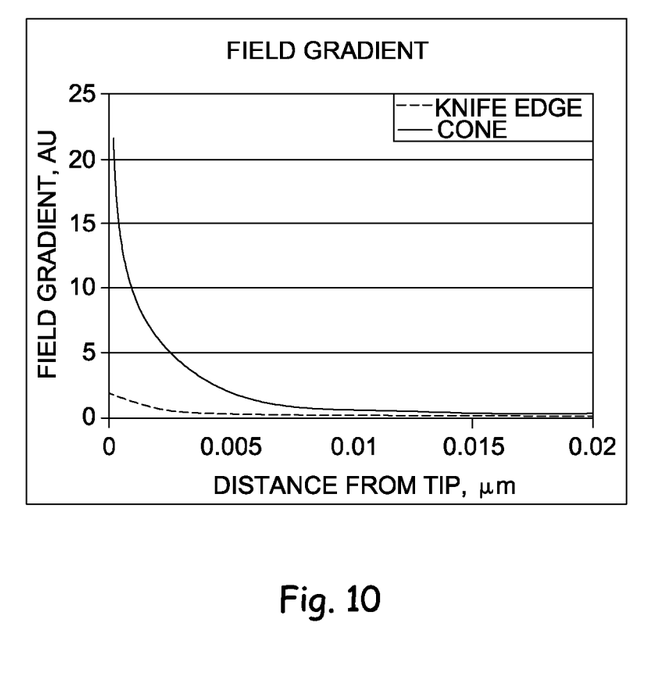
FIG. 10 is a graph comparing the simulated field gradients for the embodiment of the device including a single cone-shaped protrusion and the comparative device including a single knife-edge protrusion discussed in reference to FIGS. 4-7.

The electrostatic field and the field gradient proximate to and along the axis of the cone shaped protrusion 12' and the knife-edge protrusion are shown in FIGS. 9 and 10, respectively. At the surface of the respective tips, the magnitude of the electrostatic field and the field gradient of the cone-shaped protrusion 12' are both about eight times higher than those of the knife-edge protrusion. It is to be understood that in an actual device with many cone-shaped protrusions 12', the actual enhancement in the electric field may be affected by other geometrical parameters, such as the density, height and the angle of the protrusions 12'.

Figure 11:
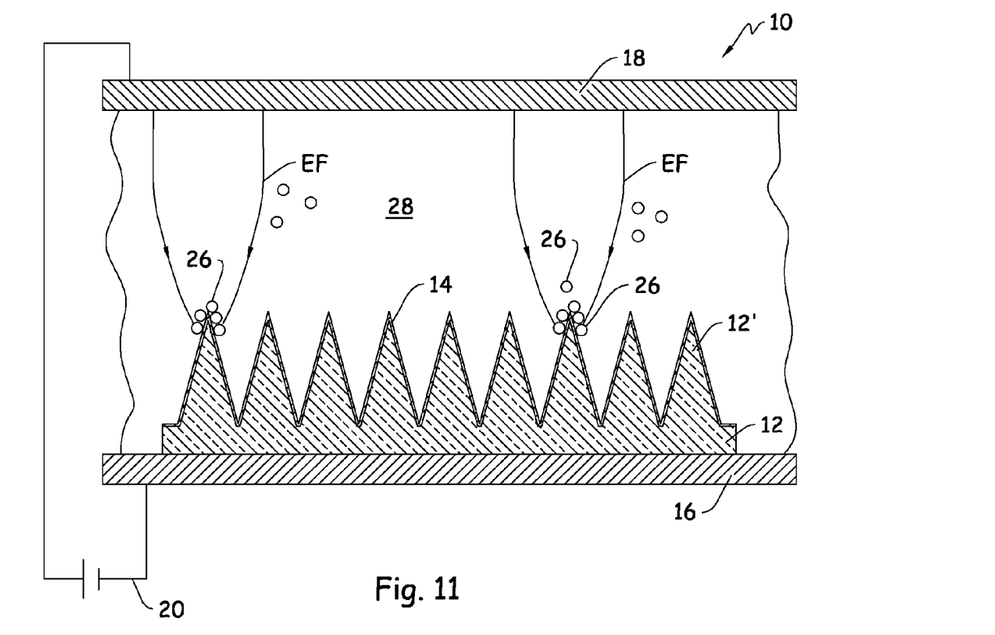
FIG. 11 is the device of FIG. 2A shown with a couple of enhanced electric fields and analyte molecules concentrated at the regions proximate the tips of the protrusions.

As mentioned hereinabove, the enhanced electrical field may be used to position an analyte molecule (or other material of interest) at the tips 22 on the surface of the substrate 12. The device 10 disclosed herein may be used to perform Raman spectroscopy on a variety of samples to identify one or more analytes. As a non-limiting example and as shown in FIG. 11, during preparation of the sample, the region between the electrode 18 and the substrate 12 with protrusions 12' is filled with a solution 28 that contains some concentration of polarizable analyte molecules 26. The analyte molecule 26 may settle on a surface of at least one of the protrusions 12' of the device 10 due to gravitational and/or chemical forces. Upon application of a voltage bias between the electrodes 16, 18 using a power source 20, the analyte molecules 26 in solution 28 are polarized and an electric field EF is generated. Application of the field EF during sample preparation increases the speed at which the analyte molecules 26 settle on the substrate 12. In the embodiments disclosed herein, the field strength increases along the path from electrode 18 to the surface S of substrate 12. The field gradient produces a net attractive force on the polarized molecules 26 toward the region proximate the tips 22 of protrusions 12'. Thus, the molecules 26 move substantially along the field lines toward the substrate 12 and attach or self-assemble in the proximities of the tips 22 of the protrusions 12' where the electric field EF and the gradient is most intense. As such, the analyte molecules 26 concentrate at the location/region proximate the tips 22.

It is to be understood that if the analyte molecules 26 have a permanent charge, they will also experience a net force and be attracted to the tips 22. Generally, positively charged molecules 26 require that the substrate 12 and/or electrode 16 be biased negatively relative to the top electrode 18, and negatively charged molecules 26 require a reversed biasing.

Furthermore, the regions with high electrostatic field, i.e., at and near the tips 22 of the protrusions 12', coincide substantially with the regions having an enhanced and high optical field when the substrate 12 is illuminated with particular optical radiation. Thus, the concentration of the analyte molecules 26 near these regions improves the SERS signal.

Figure 12:
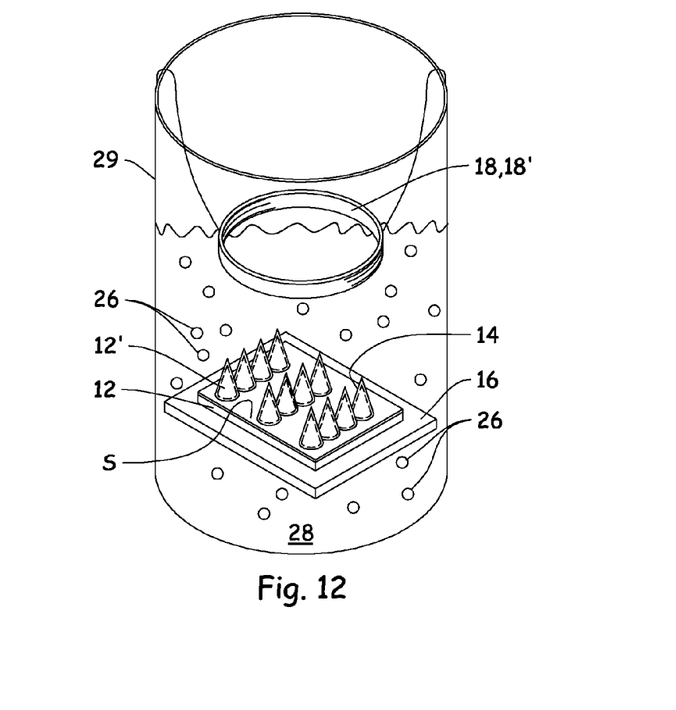
FIG. 12 is a perspective view of another embodiment of a system for surface enhanced Raman spectroscopy including an embodiment of the electrically driven device.

FIG. 12 illustrates one example of the self-assembling of the analyte molecules 26 onto the substrate 12. In this example, the substrate 12 and the electrode 16 are submersed in a solution 28 containing the analyte molecules 26, which is held in container 29. In this example, a liquid is used as the analyte carrier fluid. Non-limiting example of such liquids include water or ethanol. In other example, the carrier fluid is a gas selected from air, nitrogen, argon, or the like.

In this particular embodiment, the other electrode 18 is a hollow electrode 18' suspended over the substrate 12. It is to be understood that other embodiments of the electrode 18, 18", 18''' may also be used.

While not shown, it is to be understood that the substrate 12 is, in general, electrically connected to the bottom electrode 16 through a set of low electrical resistance contacts (e.g., a metal region on the top surface of substrate 12 or a metal bottom surface of the substrate 12 if substrate 12 is sufficiently conductive).

A solution 28 containing the analyte molecules 26 is added into the container 29 to submerse the substrate 12, the bottom electrode 16, and at least a portion of the top electrode 18. A power source 20, not shown, applies a voltage bias between the electrodes 16, 18 to generate the electric field EF in the region between the electrode 18 and the surface S of the substrate 12. The analyte molecules 26 are attracted by the electric field and/or the field gradient, and as a result they self-assemble and attach themselves proximate to the tips 22 of the protrusions 12' as previously described. After a suitable duration, the substrate 12 and electrode 16 may be removed from the container for performing the Raman spectroscopy measurement(s). It is to be understood that other methods and mechanisms for self-assembling the analyte molecules 26 to the substrate 12 may be used, including a flow through cell described hereinbelow.

Figure 13:
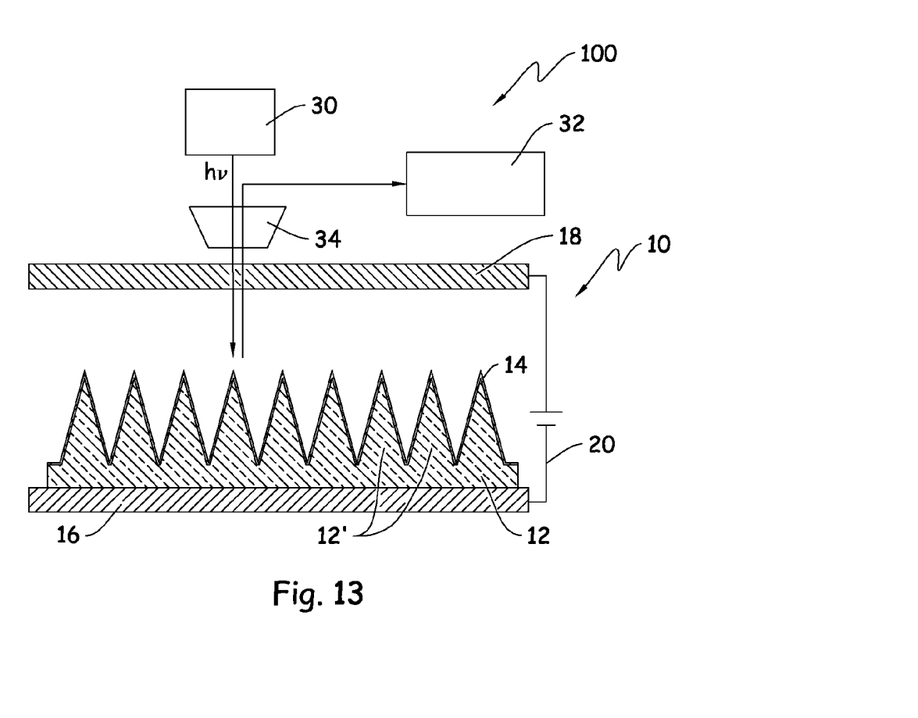
FIG. 13 is a cross-sectional and schematic diagram of an embodiment of a system for surface enhanced Raman spectroscopy including an embodiment of the electrically driven device.

Referring now to FIG. 13, an embodiment of the system 100 for performing both sample preparation and Raman spectroscopy using the device 10 is depicted. The system 100 includes at least the device 10, a stimulation/excitation light source 30, and a detector 32. A voltage bias is applied between the electrodes 16, 18 while a carrier gas or liquid containing the analyte molecules 26 flows through the space above the substrate 12. The voltage bias applied between the substrate 12/bottom electrode 16 and the top electrode 18 influences the analyte molecules to assemble proximate to the tips 22 of the protrusions 12', as described earlier.

The analyte molecules 26 (not shown in FIG. 13) and the protrusions 12' may be irradiated with electromagnetic radiation (from the light source 30), and Raman scattered radiation that is scattered by the analyte molecules 26 may be detected (using the detector 32). The increased number of molecules 26 that are exposed to the excitation wavelengths enhances the Raman signal emitted by the analyte molecules 26.

It is to be understood that the system 100 may, in some embodiments, also include an optical component 34 (e.g., an optical microscope), which is positioned between the light source 30 and the device 10. The optical component 34 focuses the light from the light source 30 to a desirable area of the substrate 12, and then again collects the Raman scattered light and passes such scattered light to the detector 32.

It is to be further understood that if desirable and in some embodiments, the top electrode 18 may be removed from the device 10 after sample preparation (i.e., concentration of the analyte molecules 26 at the tips) and prior to Raman spectroscopy measurements.

Figure 14:
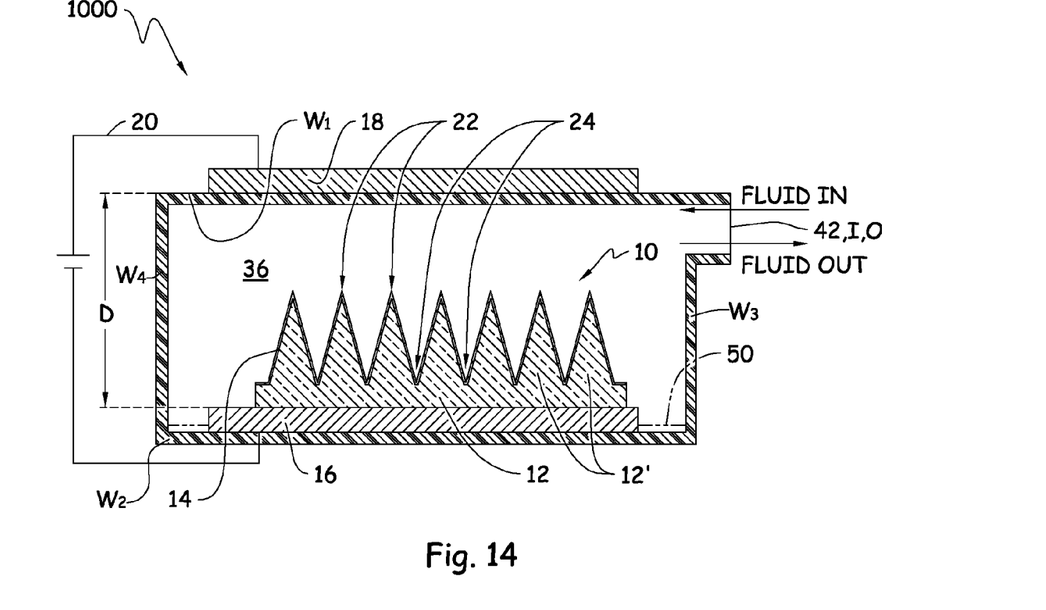
FIG. 14 is a cross-sectional and schematic diagram of an embodiment of a flow through cell having an embodiment of the electrically driven device therein.
Figure 15:
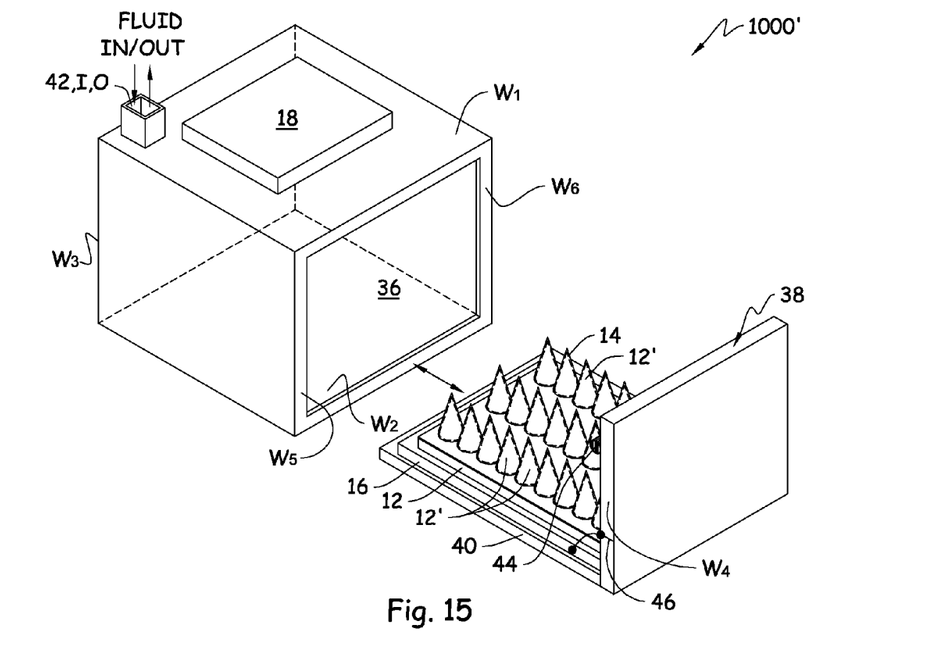
FIG. 15 is a perspective view of another embodiment of a flow through cell in which one side is removably sealable with two other sides to enclose the interior portion of the cell.

Referring now to FIG. 14, an embodiment of the device 10 is incorporated with a flow through cell 1000. The flow through device 1000 shown in FIG. 14 is a single channel cell including an enclosed interior portion 36 which defines the single channel. The enclosed interior portion 36 itself is defined by at least one surface/wall $W_1$ that is transparent to light (that will be used for Raman spectroscopy) and another surface/wall $W_2$ opposed to the at least one transparent surface $W_1$. In this embodiment, sides walls $W_3$, $W_4$ (and $W_5$, $W_6$ which are not shown in this view but are shown in FIG. 15) are attached to or formed integrally with each of the surfaces $W_1$, $W_2$ to enclose the portion 36. It is to be understood that since light is generally not introduced into the cell 1000 through the wall $W_2$ or the walls $W_3$, $W_4$, $W_5$, $W_6$, such components may be formed of transparent, semi-transparent, or opaque materials. In particular, any material may be used to form $W_2$, $W_3$, $W_4$, $W_5$, $W_6$ as long as such materials do not deleteriously affect the introduction of light into the cell 1000 or the transmission of SERS signals from the cell 1000 through the transparent wall $W_1$. In one embodiment, the regions of the wall $W_1$ that faces the light source 30 (not shown in FIG. 14) are optically smooth (e.g., there is no emission or scattering center on these surfaces and light can pass therethrough without significantly scattering (i.e., $d<\lambda/(8 \cos \theta)$, where d is the surface roughness (e.g., root-mean-square roughness height measured from a reference plane), $\lambda$ is the wavelength of the incident illumination, and $\theta$ is the angle of incidence of this illumination). As a non-limiting example, the wall $W_1$ is formed of quartz or transmissive plastics (e.g., acrylics), and the other walls $W_2$, $W_3$, $W_4$ $W_5$, and $W_6$ are formed of quartz, glass, or steel.

The dimensions of the enclosed interior portion 36 will depend, at least in part, upon the desirable dimensions of the substrate 12 that will be positioned therein. As such, the walls $W_1$, $W_2$ are spaced apart sufficiently to accommodate the substrate 12, protrusions 12', and the material 14 coated thereon. As a non-limiting example, the total thickness of the cell is the desirable distance D between the electrodes 16, 18. In one example, the total thickness of the cell 1000 is about 0.5 mm. In another example, the total thickness of the cell 1000 is up to about 5 mm. It is to be understood that the total thickness of the cell 1000 may also be limited by the working distance of the objective of the component 34 (shown in FIG. 15).

As mentioned herein in reference at least to FIG. 2A, the electrode 18 is at least partially transparent to the light to be used for Raman spectroscopy, and the other electrode 16 may or may not be transparent. It is to be understood that the electrodes 16, 18 function in the same manner as described in reference to the operation of the device 10.

As shown in FIG. 14, one of the electrodes 16 is positioned within the enclosed interior portion 36, and the other electrode 18 is positioned outside the enclosed interior portion 36. Both electrodes 16, 18 may be positioned outside of the enclosed interior portion 36. Similarly, both electrodes 16, 18 may be included within the enclosed interior portion 36. The latter configuration may be more desirable because the electrodes 16, 18 are physically closer to the substrate 12. In such instances, however, it may be desirable to establish a protective coating (not shown) over the electrodes 16, 18 in order to reduce the potential for corrosion and/or adsorption of the ions to the electrodes 16, 18. Examples of such protective electrode 16, 18 coating materials include glass, acrylic, or the like. When used to protect the electrode 18, it is to be understood that the material selected should be transparent to the excitation wavelengths and Raman signals. The protective coating is generally thin (i.e., less than 100 μm, and in some instances less than 5 nm).

The enclosed interior portion 36 includes at least one port 42 that is configured to introduce fluid (i.e., a liquid or gas containing or acting as a carrier for the analyte molecules 26) into the enclosed interior portion 36 and/or discharge the fluid from the enclosed interior portion 36. In the embodiment shown in FIG. 14, the port 42 is both a fluid inlet I and a fluid outlet O. Since the port 42 allows fluid ingress and egress, it may be fluidly coupled to a reservoir (not shown) which serves as both a sample injector and/or reaction chamber and a waste reservoir.

As shown in FIG. 14, the substrate 12 of the electrically driven device 10 is positioned in the enclosed interior portion 36. The substrate 12 includes the cone shaped protrusions 12' and the material 14 coated thereon. The materials and methods for forming the material 14 coated substrate 12 and protrusions 12' as described herein may be utilized in this embodiment as well.

As also shown in FIG. 14, the flow through cell 1000 may include a reflective layer 50 deposited on the surface $W_2$ such that it is positioned within the enclosed interior portion 36. Non-limiting examples of suitable materials for the reflective layer 50 include metals, such as silver or gold having a thickness less than or equal to 300 nm. Such a reflective layer 50 may not be desirable when a black silicon substrate 12 is used, however, the reflective layer 50 may be desirable when a substrate material is selected that is transparent to the wavelengths used during Raman spectroscopy.

Figure 16:
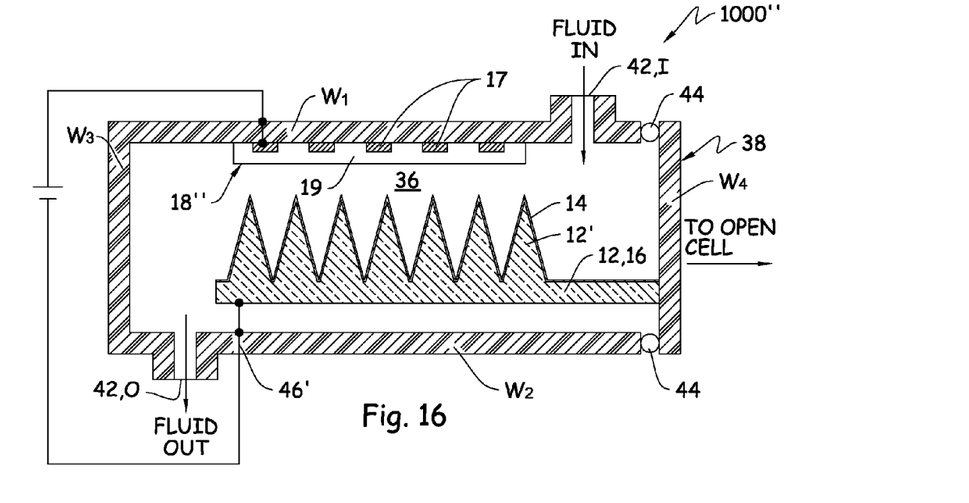
FIG. 16 is a cross-sectional view of still another embodiment of a flow through cell including an embodiment of the removably sealable one side and a partially optically transparent electrode.

Other embodiments of the flow through cell 1000', 1000" are shown in FIGS. 15 and 16. In each of these embodiments, one of the walls (e.g., wall $W_4$) is part of a carrier 38, which is detachable from the remaining structure and is removably sealable with walls $W_1$ and $W_2$ and with two of the side walls $W_5$ and $W_6$ (which are not shown in the cross-sectional view of FIG. 16). Each embodiment of the carrier 38 is moveable between an open position (as shown in FIG. 15) and a closed, sealed position (as shown in FIG. 16).

In these embodiments, the top and bottom walls $W_1$, $W_2$ are similar to those previously described.

The cells 1000', 1000" include the substrate exchange carrier 38 which supports the substrate 12 and the bottom electrode 16. In these embodiments, the side wall $W_4$ is part of the carrier 38. As shown in FIG. 15, the carrier 38 includes a support arm 40, upon which the bottom electrode 16 and substrate 12 may be positioned. In some instances, the support arm 40 also functions as the bottom wall $W_2$. As shown in FIG. 16, the carrier 38 does not include the support arm 40, but rather the substrate 12 (which, in this embodiment is also the electrode 16) is mounted to the wall $W_4$ so that when the carrier 38 is unsealed from the remainder of the cell 1000", the substrate 12 is removed from the interior portion 36. Either embodiment of the carrier 38 allows i) the substrate 12 and bottom electrode 16 to be efficiently and easily inserted into and extracted from the interior portion 36, and ii) a seal to be formed when it is in the closed position (e.g., with the assistance of one or more vacuum/fluid sealing means 44, such as an o-ring, operatively connected to the carrier 38 to seal the enclosed interior portion 36 when the carrier 38 is in the closed position).

Referring now to FIG. 15 alone, the carrier 38 includes an electrical feedthrough 46, which enables a power source 20 (not shown) to be operatively connected to the bottom electrode 16. The fluid port 42 in this embodiment is shown formed in the wall $W_1$, but it is to be understood that that the port 42 may be formed in any desirable wall $W_1$, $W_2$, $W_3$, $W_4$, $W_5$, or $W_6$ of the cell 1000'.

Referring now to FIG. 16 alone, an electrical feedthrough 46' is provided through one of the walls $W_2$ so that the power source 20 may be operatively connected to the substrate 12/bottom electrode 16 when the carrier 38 is in the closed and sealed position. It is to be understood that the feedthrough 46' may be formed in any of the walls $W_1$, $W_2$, $W_3$, $W_4$, $W_5$, or $W_6$, as long as the electrical connection made allows a voltage difference to be applied between the electrode 18 and the substrate 12/bottom electrode 16.

As illustrated, this embodiment of the cell 1000" includes the electrode 18" (previously described in reference to FIG. 3A) positioned within the enclosed interior portion 36 adjacent to the wall $W_1$. This type of electrode 18" provides the desirable electrical connection to be made and the desirable optical effects to be achieved, without having to use 100% conductive or 100% optically transparent materials. Since the electrode 18" is positioned within the cell 1000", an electrical feedthrough is provided between the conductive portion(s) 17 of the electrode 18" and the source 20.

Furthermore, in any of the embodiments disclosed herein, when the conductivity of the selected substrate 12 is sufficient to act as the electrode 16, the bottom electrode 16 may be omitted from the device 10. This is shown in FIG. 16, where the substrate 12 functions as both the substrate 12 in which the protrusions 12' are formed and the bottom electrode 16.

The inlet fluid port 42, I in the embodiment shown in FIG. 16 is shown in the wall $W_1$, and the outlet fluid port 42, O is shown in the wall $W_2$. Again, it is to be understood that that the ports 42 may be formed in any desirable wall $W_1$, $W_2$, $W_3$, $W_4$, $W_5$, or $W_6$ of the cell 1000". Furthermore, during sample preparation, it is to be understood that the port(s) 42, I, O may be sealed with any suitable plug.

Figure 17:
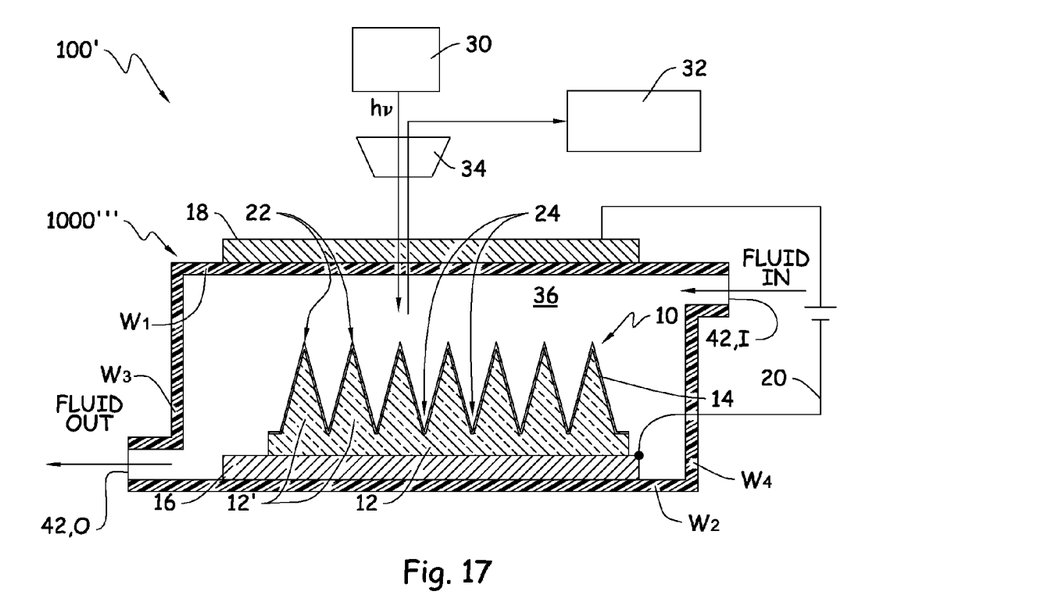
FIG. 17 is a cross-sectional and schematic view of another embodiment of a system for surface enhanced Raman spectroscopy including an embodiment of a flow through cell having an embodiment of the electrically driven device therein.

Another embodiment of a system 100' for performing Raman spectroscopy is shown in FIG. 17. This embodiment of the system 100' includes still another embodiment of the flow through cell 1000''', which includes a separate fluid inlet 42, I and fluid outlet 42, O. The inlet 42, I may be connected to one or more other devices, such as a sample injector and/or reaction chamber. The analyte molecules 26 may enter the interior portion 36 of the flow through cell 1000''' and pass across the Raman active substrate 12 (including 12' and 14), where they may be exposed to stimulating/excitation wavelengths from the light source 30, and the resulting signals may be detected by the Raman detection unit 32. In certain embodiments, the detector 32 may also be operably coupled to a computer (not shown) which can process, analyze, store and/or transmit data on analytes 26 present in the sample.

When using any embodiments of the flow through cell 1000, 1000', 1000", 1000''', it is to be understood that during sample preparation and prior to Raman analysis, the voltage bias may be applied between the electrodes 16, 18 to concentrate the analyte molecules 26 to the region proximate the tips 22 of the protrusions 12' as previously discussed in reference to the device 10.

It is to be understood that any embodiment of the flow though cell 1000, 1000', 1000", 1000''' may be used with the system 100, 100' components, including the light source 30, detector 32, and, in some instances, the optical component 34.

Figure 18:
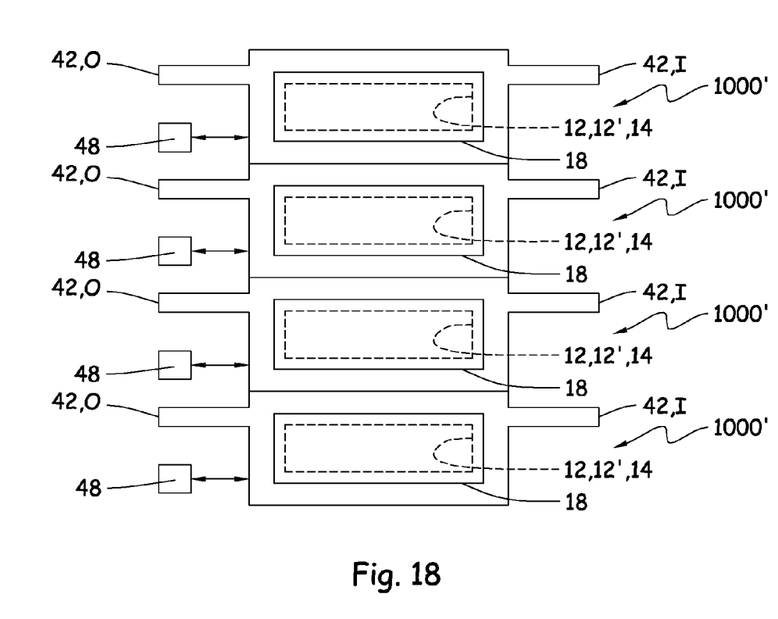
FIG. 18 is a top schematic view of still another embodiment of a system for surface enhanced Raman spectroscopy including multiple discrete flow through cells.

Referring now to FIG. 18, individual flow through cells 1000, 1000', 1000", 1000''' may be coupled together to form a multi-channel microfluidic SERS device. The single channels 1000, 1000', 1000", 1000''' may be assembled so that they are isolated from one another (i.e., have independent inlets 42, I and outlets 42, O) and are fluidly separate (i.e., the fluid in one channel does not mix with or flow to/from another channel). As a result, multiple channels are available for the simultaneous real-time detection of multiple species.

FIG. 18 also schematically depicts an ancillary device 48 operatively connected to each of the individual flow through cells 1000' in the array. The ancillary device 48 may be selected from a heater (e.g., a resistive heater, an induction heater, etc.), a cooling mechanism, a magnetic field generator, a polarizer, or combinations thereof. One or more of the flow through cells 1000, 1000', 1000", 1000''' in an array may include one or more of such devices 48. Such ancillary devices 48 may be particularly useful when the Raman signature of the analyte molecule 26 is dependent upon temperature, magnetic field, polarization of the excitation light, etc. The inclusion of the ancillary device(s) 46 inside or outside of a respective flow through cell 1000, 1000', 1000", 1000"' will depend, at least in part, on the analyte molecule 26 that is to be analyzed.

It is to be understood that any of the embodiments of the device 10 or flow through cell 1000, 1000', 1000", 1000"' disclosed herein may be fabricated as a portable unit.

Figure 19:
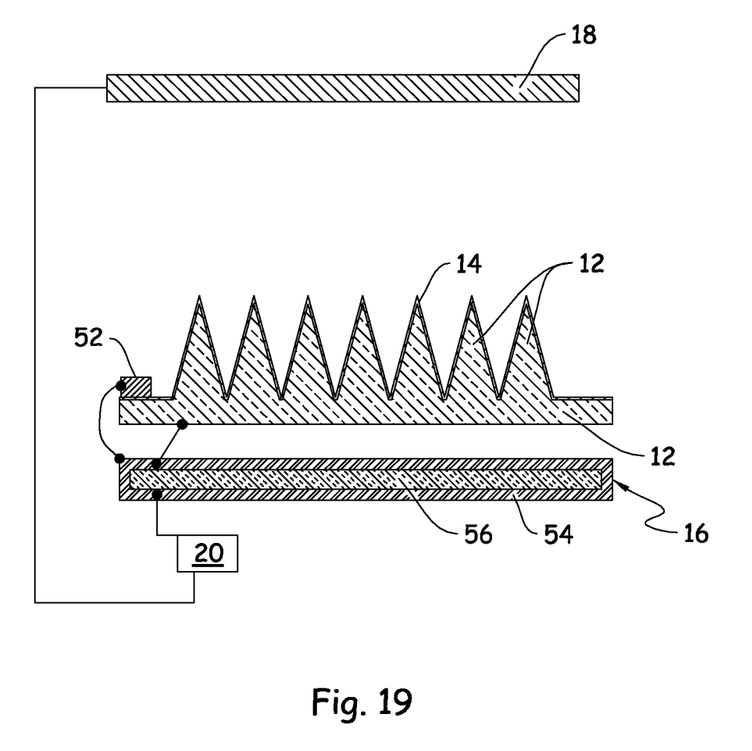
FIG. 19 is a schematic illustration of multiple electrical connections that may be used in the embodiments disclosed herein.

FIG. 19 is a cross-sectional view of the device 10 illustrating various electrical connections that can be made between the substrate 12, the bottom electrode 16, and/or the source 20. It is desirable in each of the embodiments disclosed herein that the substrate 12 be in electrical communication with the bottom electrode 16 (except of course, when the substrate 12 functions as the bottom electrode 16). Electrical connection between the substrate 12 and the electrode 16 can be made via i) a metal contact 52 positioned adjacent a flat portion of the substrate 12 in contact with the material 14 in combination with some mechanism operably connecting the contact 52 to the electrode 16, ii) the conductive substrate 12 sitting directly on the conductive electrode 16 (or directly on a conductive layer 54 surrounding an insulator 56, as shown in FIG. 19), or iii) a wire clip operably connecting the substrate 12 to the electrode 16. While wire clips are shown in FIG. 19, it is to be understood that any other mechanism that enables electrical communication between the substrate 12 and the electrode 16 may be used (e.g., solder joints). Since wire clips may be used to electrically connect the substrate 12 and the electrode 16, in some instances, the substrate 12 may be floating in a solution that contains the analyte molecules 26. Electrical connection between the substrate 12 and the electrode 16 via any path that is electrically conductive or semi-conductive.

Furthermore, while not shown, it is to be understood that the embodiments of the device 10 disclosed herein may further include a binding material that is configured to bind a selected analyte molecule 26 to the protrusion 12' at a location where a strong localized electrical field EF may be induced. In one embodiment, such a binding material may be particularly suitable for disposal proximate one or more of the crevices 24. The binding material may include any material to which a selected analyte molecule 26 will preferably bind relative to the protrusions 12'. Alternatively, the binding material may include molecules that, together with the selected analyte, form what is known in the art as a "specific pair" or a "recognition pair" of molecules. As a non-limiting example, if the selected analyte is an antigen or an antibody, the binding material may be a complementary antigen or antibody. Many biomolecules act as receptors or ligands to other biomolecules. If the selected analyte is or includes such a biomolecule, the binding material may include a complementary biomolecule.

When the aforementioned binding material is included in the device 10, it is generally desirable that the analyte molecule 26 selected will have a propensity to bind to the binding material. This analyte molecule 26 may be provided on a surface of the substrate 12. The analyte molecule 26 may be attracted to the binding material, and the binding material may hold or bind the analyte in or proximate to the crevice(s) 24 at which the binding material is present. The analyte molecule 26 and the substrate 12 may be irradiated with electromagnetic radiation, and the Raman scattered radiation that is scattered by the analyte molecule 26 may be detected. Since the binding material holds the analyte molecule 26 in the crevice(s) 24, the Raman signal emitted by the analyte molecule 26 may be enhanced.

As set forth herein, the unique combination of the material 14 covered protrusions 12' having the desirable radius of curvature and the electrodes (placed at a desirable distance D from each other) enable a significantly enhanced electric field to be generated at very specific portions of the device 10, which, in turn, advantageously enhances SERS signals.

While several embodiments have been described in detail, it will be apparent to those skilled in the art that the disclosed embodiments may be modified. Therefore, the foregoing description is to be considered exemplary rather than limiting.

What is claimed is:

1. A system for surface enhanced Raman spectroscopy, comprising:
   a flow through cell, including:
      an enclosed interior portion defined by at least one wall that is transparent to light having a wavelength of interest and an other wall opposed to the at least one transparent wall; and
      at least one port configured to at least one of introduce fluid into the enclosed interior portion or discharge the fluid from the enclosed interior portion;
   an at least partially transparent electrode established adjacent to the at least one transparent wall of the flow through cell, the at least partially transparent electrode being at least partially transparent to the light having the wavelength of interest;
   an electrically driven device positioned within the enclosed interior portion, the electrically driven device including:
      a substrate having a plurality of cone shaped protrusions formed integrally with a surface thereof, each of the plurality of cone shaped protrusions having a tip with a radius of curvature ranging from about 5 nm to about 1000 nm; and
      a Raman signal-enhancing material coated on each of the plurality of cone shaped protrusions, the Raman signal-enhancing material facing the at least one transparent wall of the flow through cell; and
   a second electrode positioned relative to the transparent electrode at a predetermined distance such that the electrodes together produce, when a voltage bias is applied, an electric field having a field distribution that creates a stronger field gradient at a region proximate to the tip of each cone shaped protrusion than at other portions of the substrate.

2. The system as defined in claim 1 wherein the enclosed interior portion is further defined by four side walls, one of the four side walls being removably sealable with two other of the four side walls, and the one of the four side walls having a support arm connected thereto, the support arm configured to support the second electrode and the substrate within the enclosed interior portion when the one of the four side walls is sealed with the two other of the four side walls.

3. The system as defined in claim 1, further comprising a plurality of flow through cells coupled together, each of which has an electrically driven device positioned therein, and each of which is fluidly separate from each other flow through cell.

4. The system as defined in claim 1, further comprising an ancillary device operatively imbedded in or attached to the flow through cell, the ancillary device selected from a heater, a cooling mechanism, a magnetic field generator, a polarizer, or combinations thereof.

5. The system as defined in claim 1, further comprising a reflector positioned on the other wall that is opposed to the at least one transparent wall of the flow through cell.

6. The system as defined in claim 1 wherein the substrate is the second electrode.

7. The system as defined in claim 1 wherein the substrate is selected from single crystalline silicon, polymers, glass, silicon nitride, quartz, ceramics, sapphire, and metals.

8. The system as defined in claim 1 wherein the field distribution includes electric field lines converging and concentrating at the region proximate to the tip of each of each cone shaped protrusion, and wherein analyte molecules dispersed in a liquid or gas carrier that is introduced to a region between the second electrode and the substrate, under influence of the electric field and gradient, concentrate at the region proximate to the tip of each cone shaped protrusion.

9. The system as defined in claim 1 wherein:
the at least partially transparent electrode is positioned outside of the enclosed interior portion and the second electrode is positioned within the enclosed interior portion; or
both the at least partially transparent electrode and the second electrode are positioned outside of the enclosed interior portion; or
both the at least partially transparent electrode and the second electrode are positioned within the enclosed interior portion.

10. The system as defined in claim 1 wherein a crevice is present between adjacent cone shaped protrusions, and wherein an optical field is enhanced at each crevice upon exposure of the electrically driven device to an optical illumination.

11. The system as defined in claim 1, further comprising:
a power source operatively connected to the at least partially transparent electrode and the second electrode and configured to apply the voltage bias between the electrodes;
a light source operatively configured to direct light toward the surface of the substrate; and
a detector operatively positioned to detect an enhanced Raman signal from a material of interest concentrated at the regions proximate to the tips.

* * * * *